(12) United States Patent
Xu

(10) Patent No.: US 10,706,536 B2
(45) Date of Patent: Jul. 7, 2020

(54) PHOTON STRUCTURE AND CHEMOMETRICS PATHOLOGIC SYSTEM

(71) Applicant: Min Xu, Zhejiang (CN)

(72) Inventor: Min Xu, Zhejiang (CN)

( * ) Notice: Subject to any disclaimer, the term of this patent is extended or adjusted under 35 U.S.C. 154(b) by 355 days.

(21) Appl. No.: 15/746,356

(22) PCT Filed: Jul. 20, 2016

(86) PCT No.: PCT/CN2016/090755
§ 371 (c)(1),
(2) Date: Jan. 19, 2018

(87) PCT Pub. No.: WO2017/012555
PCT Pub. Date: Jan. 26, 2017

(65) Prior Publication Data
US 2020/0143531 A1 May 7, 2020

Related U.S. Application Data

(60) Provisional application No. 62/194,462, filed on Jul. 20, 2015.

(51) Int. Cl.
G06K 9/00 (2006.01)
G06T 7/00 (2017.01)
G01N 21/64 (2006.01)

(52) U.S. Cl.
CPC ....... G06T 7/0012 (2013.01); G01N 21/6458 (2013.01); G01N 21/6486 (2013.01);
(Continued)

(58) Field of Classification Search
CPC .......................................... G06T 2207/30096
See application file for complete search history.

(56) References Cited

U.S. PATENT DOCUMENTS

2005/0065440 A1 3/2005 Levenson
2011/0117025 A1 5/2011 Dacosta et al.
(Continued)

FOREIGN PATENT DOCUMENTS

CN 1317688 A 10/2001
CN 102099671 A 6/2011
(Continued)

OTHER PUBLICATIONS

Kong et al Phase contrast microscopy of living cells within the whole lens: spatial correlations and morphological dynamics Received Mar. 18, 2012 | Accepted Jul. 28, 2012 | Published Aug. 1, 2012 (Year: 2012).*

*Primary Examiner* — Oneal R Mistry
(74) *Attorney, Agent, or Firm* — Christensen, Fondor, Dardi & Herbert PLLC

(57) ABSTRACT

A photonic structural and chemometric pathology system for cancer and precancerous or general detection, diagnosis, monitoring and prognosis utilizes fresh or frozen tissue standard pathology sections without prior as staining or other labeling techniques. The unlabeled tissue section may be imaged, with a phase and fluorescence imaging microscope, to obtain phase differential contrast (Q-DIC) images and fluorescence images. The Q-DIC images are analyzed to generate two dimensional Q-DIC data maps, such as morphology, cell mass, and scattering characteristic digital image maps. The fluorescence images are analyzed to generate fluorescence intensity and tissue native fluorescent component absolute concentration maps. The combination of Q-DIC data maps and fluorescent component content maps is comparatively analyzed to perform cancer and pre-cancerous or general diagnosis and prognosis. The system can be applied to a wide range of cancers and tissues for
(Continued)

noninvasive and unlabeled cancer and pre-cancerous or general detection, diagnosis, monitoring and prognosis.

**9 Claims, 7 Drawing Sheets
(6 of 7 Drawing Sheet(s) Filed in Color)**

(52) U.S. Cl.
CPC .................. *G01N 2201/129* (2013.01); *G06T 2207/10056* (2013.01); *G06T 2207/10064* (2013.01); *G06T 2207/20048* (2013.01); *G06T 2207/30024* (2013.01); *G06T 2207/30061* (2013.01); *G06T 2207/30081* (2013.01); *G06T 2207/30096* (2013.01)

(56) References Cited

U.S. PATENT DOCUMENTS

| | | | |
|---|---|---|---|
| 2011/0254943 A1* | 10/2011 | Ozinsky | G01N 21/6458 348/79 |
| 2014/0050386 A1* | 2/2014 | Humayun | A61L 27/38 382/133 |
| 2014/0119628 A1 | 5/2014 | Elad et al. | |
| 2014/0205057 A1 | 7/2014 | Koehler et al. | |
| 2014/0268168 A1 | 9/2014 | Feldman et al. | |
| 2016/0266126 A1* | 9/2016 | Shipitsin | C12Q 1/6886 |

FOREIGN PATENT DOCUMENTS

| CN | 102266219 A | 12/2011 |
|---|---|---|
| CN | 103918005 A | 7/2014 |

\* cited by examiner

FIG. 3 $\quad k\frac{\partial I}{\partial z} = -I\nabla_\perp^2 \phi \quad$ Equation (1)

FIG. 4 $\quad -\nabla_\perp^2 \phi = k\frac{\partial Ln I}{\partial z} = k\frac{Ln I_1 - Ln I_2}{\partial z} \quad$ Equation (2)

FIG. 5 $\quad \mu'_s L = 2(1 - \cos\Delta\phi)$ $\qquad$ Equation (3)

FIG. 6 $\quad \mu'_s L = \dfrac{1}{2k^2}\langle |\nabla\phi|^2 \rangle$ $\qquad$ Equation (4)

FIG. 7 $\quad g = 1 - \dfrac{\langle |\nabla\phi|^2 \rangle}{4k^2(1-\cos\Delta\phi)}$ $\qquad$ Equation (5)

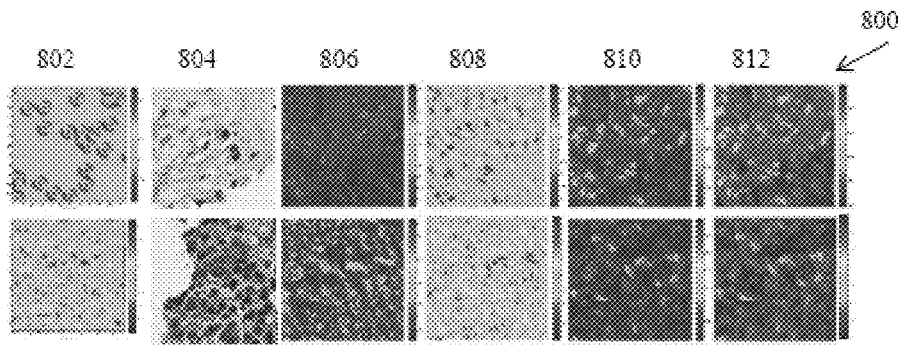

FIG. 8

|  | Polystyrene microspheres | | | Intralipid-20% suspension | | |
|---|---|---|---|---|---|---|
|  | $c_{sca}(\mu m^{-1})$ | $c'_{sca}(\mu m^{-1})$ | g | $\mu_s(\mu m^{-1})$ | $\mu'_s(\mu m^{-1})$ | g |
| Theoretical | 125 | 9.5 | 0.92 | 0.139 | 0.031 | 0.78 |
| Measured | 118 | 10.2 | 0.91 | 0.136 | 0.022 | 0.84 |

FIG. 9

$$\begin{pmatrix} I_1 \\ I_2 \\ \vdots \\ I_m \end{pmatrix} = \begin{pmatrix} w_{11} & w_{12} & \cdots & w_{1n} \\ w_{21} & w_{22} & \cdots & w_{2n} \\ \vdots & \vdots & \ddots & \vdots \\ w_{m1} & w_{m2} & \cdots & w_{mn} \end{pmatrix} \begin{pmatrix} C_1 \\ C_2 \\ \vdots \\ C_n \end{pmatrix} \qquad \text{Equation (6)}$$

FIG. 10

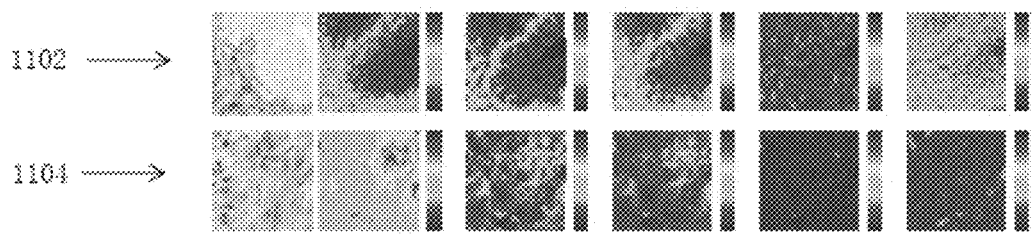

FIG. 11

| | $\mu_s'(\mu m^{-1})$ | $OPL(\mu m^{-1})$ | g | Tryptophan | NADH | FAD | FAD/TRY | FAD/NADH |
|---|---|---|---|---|---|---|---|---|
| Normal | 0.045(0.018) | 1.17(0.21) | 0.85(0.05) | 330(160) | 5.1(1.9) | 0.13(0.05) | 4.5(3.5)×10⁻⁴ | 29(9)×10⁻³ |
| Cancerous | 0.040(0.014) | 1.10(0.13) | 0.85(0.06) | 520(160) | 6.6(1.0) | 0.15(0.05) | 3.2(1.2)×10⁻⁴ | 24(4)×10⁻³ |
| P-value | 0.6 | 0.2 | 1 | 0.001 | 0.004 | 0.2 | 0.01 | 0.03 |

| | $\mu_s'(\mu m^{-1})$ | $OPL(\mu m^{-1})$ | g | Tryptophan | NADH | FAD | FAD/TRY | FAD/NADH |
|---|---|---|---|---|---|---|---|---|
| PSA NRec | 0.038(0.014) | 1.07(0.22) | 0.863(0.056) | 410(260) | 4.7(2.2) | 0.09(0.04) | 2.9(1.8)×10⁻⁴ | 22(6)×10⁻³ |
| PSA Rec | 0.046(0.011) | 1.24(0.21) | 0.828(0.022) | 390(200) | 5.0(2.7) | 0.11(0.05) | 3.2(1.8)×10⁻⁴ | 24(8)×10⁻³ |
| P-value | 2×10⁻⁴ | 6×10⁻⁵ | 4×10⁻³ | 0.6 | 0.6 | 0.6 | 0.4 | 0.2 |

| | Tryptophan | Elastin | NADH | FAD | FAD/Tryptophan | FAD/NADH |
|---|---|---|---|---|---|---|
| Normal | 63(15) | 23(19) | 1.02(0.40) | 0.43(0.13) | 7.6(1.8)×10⁻³ | 0.63(0.28) |
| Perilesional | 44(10) | 13(7) | 0.64(0.15) | 0.33(0.13) | 8.4(2.2)×10⁻³ | 0.75(0.38) |
| Cancerous | 24(8) | 9.1(4.9) | 0.41(0.11) | 0.14(0.05) | 6.5(2.5)×10⁻³ | 0.38(0.15) |
| P-value N-P | 4×10⁻⁵ | 0.006 | 1×10⁻⁵ | 0.01 | 0.6 | 0.3 |
| P-C | 8×10⁻¹² | 9×10⁻⁴ | 1×10⁻⁹ | 3×10⁻¹⁵ | 0.005 | 7×10⁻⁷ |
| N-C | 1×10⁻¹⁹ | 3×10⁻⁷ | 1×10⁻¹⁶ | 1×10⁻¹⁹ | 0.009 | 0.0001 |

PHOTON STRUCTURE AND CHEMOMETRICS PATHOLOGIC SYSTEM

TECHNICAL FIELD

The present invention relates to human cancer diagnostic systems and, more particularly, to a photonic structural and chemometric pathology system utilizing unlabeled tissue sections for cancer and pre-cancerous detection, diagnosis, monitoring, and prognosis.

BACKGROUND

There are a wide range of conventional approaches to cancer and precancerous detection, diagnosis, monitoring, and prognosis. Techniques involving tissue analysis generally utilize tissue sections that are stained or otherwise labeled to increase the contrast of effected areas. Preparing the sections for analysis usually requires time consuming processing including the application stain or other labeling techniques that obscure some aspects of the sample. At present, there are not effective cancer detection and diagnostic techniques available that utilize fresh or frozen tissue sections without prior processing, such as staining or other labeling techniques. This delays and complicates the detection and diagnostic process and makes the process more expensive while also limiting the pathology lab from processing more samples and generating more revenue.

The current pathology practice using conventional light microscopy has several critical limitations, including a) time consuming and costly multiple step tissue processing is required to prepare the sample; b) the lateral resolution is about 0.5 mm or worse and no axial information of the specimen is revealed; and c) the diagnosis based mainly on the manual expert examination of the tissue architectural and morphological changes is subjective and suffers from inter- and intra-observer variations. The PSCP system addresses all the above limitations while achieving a cost effective and objective means of higher accuracy for rapid cancer diagnosis and prognosis.

The issue of overtreatment of prostate cancer has received wide public attention demonstrating a need for better prognostication at time of diagnosis. This challenge results partially from the limited sampling of the cancer and therefore limited routine microscopic clues on the diagnostic needle biopsy. Evolving efforts are being made to determine a gene based score to address this need. With the state-of-the-art risk scoring based on co-registered structural and molecular signatures, PSCP offers better prognosis for determination of need for therapy. Identifying and treating only those cancers which will become clinically significant will considerably reduce the treatment costs and the economic burden of cancer.

There is, therefore, a continuing need for improved cancer and precancerous detection, diagnosis, monitoring, and prognosis techniques. More specifically, there is a continuing need for cancer diagnostic techniques that utilize fresh or frozen tissue sections without requiring time consuming prior staining or other labeling techniques prior to analysis of the tissue sections.

SUMMARY

The present invention provides a method for quantifying a microstructure of a biological tissue by utilizing light interaction, which comprises steps of imaging tissue sections with a phase imaging microscope to obtain a Q-DIC image, and analyzing the Q-DIC image to obtain a two-dimensional Q-DIC quantitative map, and thereby the obtained accurate quantitative map can be used for detecting somatic functions of human bodies, including but not limited to detection, diagnosis and prognosis of pathologies and cancers, with an advantage of being quick and accurate.

The present invention also provides a method for quantifying a molecular content of a biological tissue by utilizing the auto-fluorescence thereof, which comprises steps of imaging a tissue section with a fluorescence imaging microscope to obtain a fluorescence microscope image, and computing and factorizing the fluorescence microscope image by the following equation to obtain a fluorescent component data map:

$$\begin{pmatrix} I_1 \\ I_2 \\ M \\ I_m \end{pmatrix} = \begin{pmatrix} w_{11} & w_{12} & \Lambda & w_{1n} \\ w_{21} & w_{22} & \Lambda & w_{2n} \\ M & M & O & M \\ w_{m1} & w_{m2} & \Lambda & w_{mn} \end{pmatrix} \begin{pmatrix} C_1 \\ C_2 \\ M \\ C_m \end{pmatrix} \quad \text{Equation (6)}$$

(wherein, I is the fluorescence intensity, w is the weight factor, and C is the content of a fluorescent substance)

With this method, absolute content of fluorescent molecules and a distribution map thereof can be obtained for quick and accurate detection of somatic functions of human bodies, including but not limited to detection, diagnosis and prognosis of pathologies and cancers.

The present further provides a photonic structural and chemometric pathology system for cancer detection, diagnosis, monitoring and/or prognosis that utilizes standard pathology sections without prior staining or other labeling techniques. The same unlabeled tissue section may be imaged, in some cases with the same phase imaging microscope, to obtain phase differential contrast (Q-DIC) images and fluorescence images. The Q-DIC images are analyzed to generate two dimensional Q-DIC quantitative maps, such as morphology, cell mass, and scattering data maps. The fluorescence images are analyzed to generate fluorescence intensity, fluorescence molecular content and metabolism data maps. The combination of Q-DIC and fluorescence intensity digital data maps are then analyzed individually and comparatively to perform cancer diagnosis and prognosis. The system is useful for a wide range of cancers including solid and fibrous tumors and is particularly well suited for providing detection, diagnosis, monitoring and/or prognosis for prostate cancer, lung cancer, breast cancer, etc.

The Q-DIC data maps and fluorescence intensity digital image maps are co-registered, for example (but not necessarily) on a pixel-by-pixel basis, to facilitate image comparison. The co-registered digital image maps may be visually compared side-by-side and in overlay format. Computational analysis may also be performed to data maps individually and comparatively. A prior diagnostic database of Q-DIC data maps and fluorescence intensity maps correlated to known pathology is analyzed to produce a risk assessment scoring methodology, which is applied to patient Q-DIC data maps and fluorescence intensity maps to obtain cancer detection, diagnosis monitoring and/or prognosis.

This approach has the advantage of producing diagnostic and prognostic results within a matter of minutes using fresh or frozen tissue sections that do not have to be stained or otherwise labeled for analysis. Appropriate Q-DIC images and fluorescent images can be obtained from standard pathology sections using a conventional phase and fluorescence imaging microscope. A software application containing the image analysis and risk scoring methodology can be installed and run on any suitable computer, such as a desktop, laptop, server or other computing device. In many cases, the diagnostic system may be cost effectively installed in a medical office, lab, or hospital to provide cancer diagnostic and prognostic results within a matter of minutes during a single patient appointment. This approach also produces a more objective method for cancer detection by removing elements of subjective analysis from interpretations by a human pathologist.

BRIEF DESCRIPTION OF THE DRAWINGS

The patent application contains at least one drawing executed in color. Copies of this patent with color drawing(s) will be provided by the Patent and Trademark Office upon request and payment of the necessary fee.

FIG. 3 shows equation (1).

FIG. 4 shows equation (2).

FIG. 5 shows equation (3).

FIG. 6 shows equation (4).

FIG. 7 shows equation (5).

FIG. 8 shows a first set of images.

FIG. 9 shows a first table comparing measured image parameters to theoretical image parameters.

FIG. 10 shows equation (6).

FIG. 11 shows a second set of images comparing normal to cancerous images.

DETAILED DESCRIPTION

Embodiments of the invention may be realized in a photonic structural and chemometric pathology (PSCP) system for cancer detection, diagnosis, monitoring and/or prognosis that utilizes standard pathology sections from fresh or frozen human tissue without prior staining or other labeling techniques. The appended figures along with the attached slide presentation, which form part of this disclosure, are summarized and referenced below.

The PSCP system is a novel cost-effective, label-free, quantitative, real-time tissue structural and molecular pathology tool for cancer diagnosis and prognosis. Current histopathology, which mainly utilizes the degree of loss of the normal glandular tissue architecture for cancer diagnosis, is subjective and suffers from inter- and intra-observer variations and has difficulty in distinguishing aggressive cancers from indolent ones. PSCP utilizes alternate clues including alterations in tissue structure and cellular metabolism to achieve an objective risk stratification of cancer grade and aggressiveness and may prove a reliable adjunct or an independent system for rapid diagnostic and prognostic assessment.

The PSCP system provides a novel, cost-effective, label-free, quantitative real-time tissue structural and molecular pathology for cancer diagnosis and prognosis. The system integrates quantitative phase imaging and tissue native fluorescence imaging to simultaneously quantify at the cellular and subcellular level the morphology, mass distribution, scattering characteristics, and metabolism of standard, unlabeled pathology tissue sections. Co-registered two dimensional (2D) microscopic maps of tissue morphology, mass distribution, scattering characteristics, and distribution of native fluorescence molecules and metabolism of cancer tissue sections are correlated with histopathology and patient outcomes. Based on these correlations, a risk stratification algorithm based on a state-of-the-art support vector machine (SVM) for identifying the risk score for a patient is utilized to grade cancer and predict patient outcome. The PSCP system integrates spatially-resolved tissue structural and molecular imaging for cancer diagnosis and prognosis for the first time to overcome major challenges faced by conventional pathology including inter- and intra-observer variations related to the subjective diagnosis based on mainly tissue morphology and the difficulty of distinguishing aggressive cancers from indolent ones. Furthermore, PSCP is label-free and can achieve real-time diagnosis by directly analyzing fresh or frozen unstained tissue.

Figure 1:
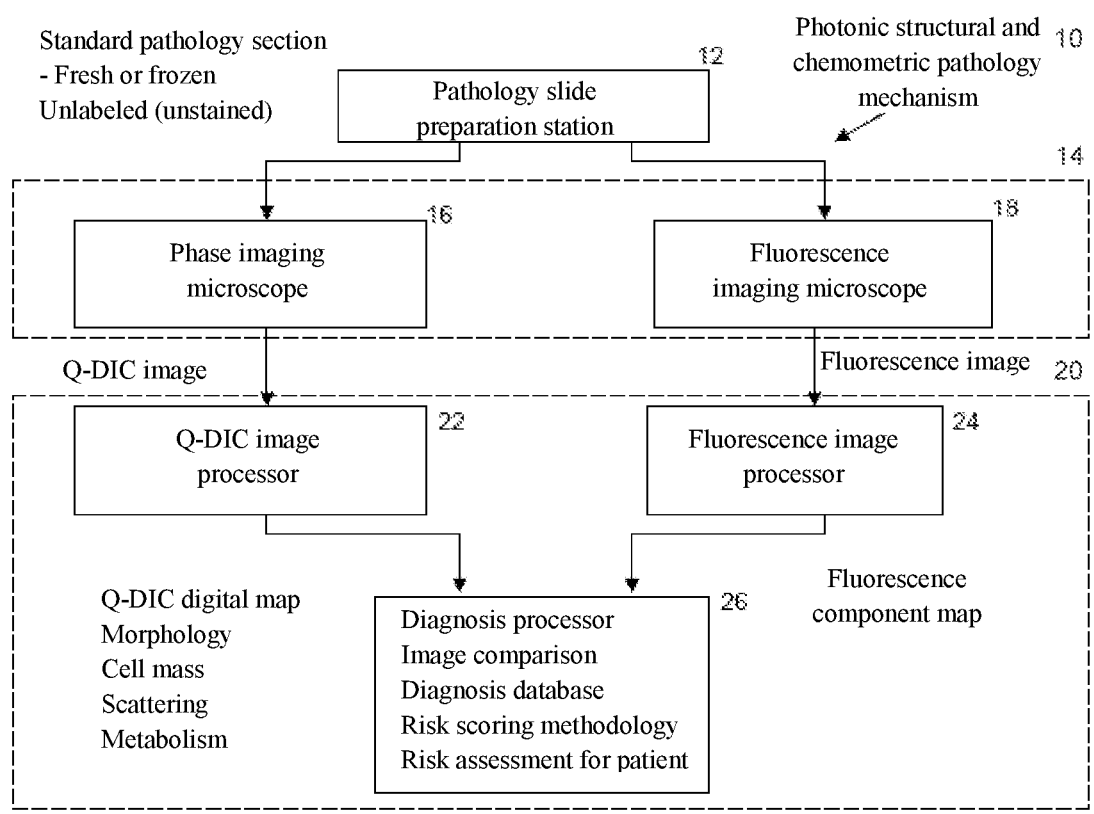
FIG. 1 is a block diagram of a photonic structural and chemometric pathology system.

FIG. 1 is a block diagram of the photonic structural and chemometric pathology (PSCP) system 10. The system may be implemented using a standard pathology slide preparation station 12, a standard phase imaging microscope 14 with fluorescent imaging capability, and a specially configured general purpose computer 20. The slide preparation station 12 is used to prepare a standard pathology section, which may be prepared from a fresh or frozen tissue specimen. The section is typically 4 to 5 microns thick and need not be stained or otherwise labeled, which avoids the usual need for time consuming slide preparation, such as section staining.

The same tissue slide can be used to create both Q-DIC and fluorescence images. This feature is available in the conventional phase imaging microscope available in many medical offices, labs and hospitals. The Q-DIC and fluorescence images are input into a computer system 20, which may be any suitable general purpose computer configured with software to perform the innovative image processing and diagnostic methodology. More specifically, the computer system 20 includes a QDIC image processor 22 that computes a variety of two dimensional Q-DIC quantitative maps from the base Q-DIC images, such as morphology, cell mass, and scattering characteristic digital data maps. The computer system 20 also includes a fluorescence image processor 24, which computes a content of fluorescent molecules and metabolism digital data map from the fluorescence image. The Q-DIC, fluorescence and their derivative digital data maps are then passed to a diagnostic processor 26 for diagnostic and prognostic analysis.

The Q-DIC and fluorescence digital data maps may be co-registered on a pixel-by-pixel basis to adjust the sizes to provide maps of similar size for comparison. The digital data maps may also be placed side-by-side for visual analysis, placed in an overlay mode for visual analysis, and subjected to individual image and comparative computational analysis. The diagnostic processor 26 also includes a risk assessment scoring methodology and may also include a prior diagnostic database of Q-DIC and fluorescent component data maps for patients with known pathology used to create the risk assessment methodology. Regardless of whether the database itself is included on a particular embodiment, the risk assessment scoring methodology is applied to patient Q-DIC and fluorescent component data maps obtained from a particular tissue sample to produce diagnostic and prognostic results for the patient associated with the tissue sample.

In an illustrative embodiment, the pathology slide preparation station 12 may be any suitable type of slide preparation station and, in many cases, the slides arrive at the analysis location from cold storage or another location. The QDIC microscope may generally be an inverted brightfield, phase contrast, differential interference contrast, and fluorescence microscope with a focus drive.

Figure 2:
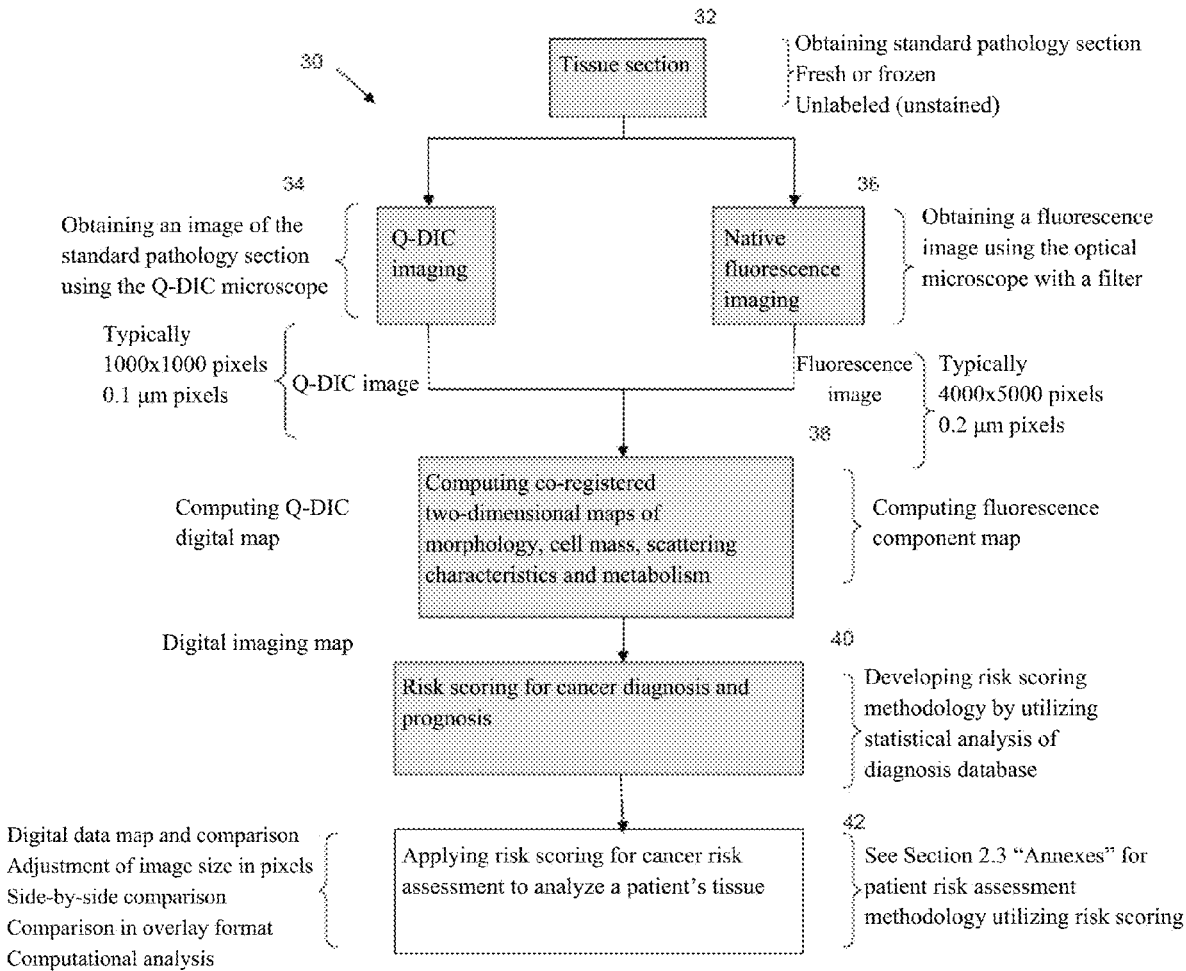
FIG. 2 is a logic diagram of a method for performing cancer diagnosis and prognosis using the photonic structural and chemometric pathology system and standard, unlabeled pathology tissue sections.

FIG. 2 is a logic diagram of a method 30 for performing cancer diagnosis and prognosis using the photonic structural and chemometric pathology system and standard, unlabeled pathology tissue sections. In block 32, a standard pathology section is prepared using a tissue sample obtained from a patient. For example, a fresh or frozen, unlabeled (unstained) tissue section may be utilized. In block 34, a phase differential imaging microscope is used to obtain a Q-DIC image of the tissue section.

In block 36, a fluorescence microscope is used to obtain a native fluorescence image of the tissue section. The Q-DIC image and fluorescence image are typically obtained using different settings of the same phase imaging microscope and a fluorescence filter for the fluorescence image.

In block 38, the Q-DIC image is processed to obtain a variety of Q-DIC quantitative maps, such as morphology, cell mass, and scattering characteristic digital data maps. Also in block 38, the fluorescence image is processed to obtain fluorescence intensity, native fluorescence molecular content and metabolism digital data maps. In block 40, a historical database of Q-DIC data maps and fluorescence intensity data maps for subjects with known pathology is analyzed to identify correlations between the map data and pathology diagnosis and prognosis. These correlations are typically reduced to a risk scoring methodology allowing higher risk cancers to be identified based on individual and comparative data map characteristics. The risk scoring methodology includes a range of predictive characteristics, combinations of characteristics, and overall profiles based on analysis of the historical database, which is refined through experience using the system. The effectiveness of the risk scoring methodology is expected to improve as the size and analytical detail of the database increases. It will therefore be beneficial to obtain a large initial data set and continually augment the database as experience with the system develops. The risk scoring methodology may also be adapted to score different types of cancer, different types of tissue, and other variations found to be effective through use and vetting of the system and associated database.

In block 42, the risk scoring methodology is applied to the data obtained from a particular tissue section to obtain specific diagnostic and prognostic results. Since the system utilizes standard pathology sections imaged with a standard phase imaging microscope analyzed with software configured on a general purpose computer, specific diagnostic and prognostic results can be obtained for a patient within minutes utilizing widely available equipment, in many cases within the same appointment where the tissue sample is obtained.

The PSCP system thus integrates quantitative phase imaging and tissue native fluorescence imaging to simultaneously quantify at the cellular and subcellular level the morphology, mass distribution, scattering characteristics, native fluorescence molecular content and metabolism of tissue without any prior tissue staining or other label processing. Co-registered two dimensional (2D) microscopic tissue structural and molecular maps of cancer tissue sections are correlated with histopathology and patient outcomes. Based on these correlations, a risk stratification algorithm for identifying the risk score for a patient is utilized to grade cancer and predict patient outcome. The PSCP system thereby integrates spatially-resolved tissue structural and molecular imaging for cancer diagnosis and prognosis for the first time.

The PSCP approach uses light scattering to sense the sub-wavelength changes in the microenvironment and probes native fluorescent molecules and cellular metabolism based on the auto-fluorescence of biological tissues. Light scattering has been demonstrated to be sensitive to nuclear and cellular alterations as small as a few nanometers and has been successfully applied to detect early carcinoma undetectable by conventional methods. Tissue native fluorescence has also been shown to be an effective probe for tissue physiological state, be it oxidative stress, metabolism, cell growth and cell survival or death.

The PSCP approach extracts objectively the 2D maps of the inherent tissue 3D structural and molecular characteristics directly from light interaction with intact tissue, avoiding subjective human interpretation and post-image pattern analysis (in digital pathology) of microscopic images of stained samples. Compared with auto-fluorescence spectroscopy, the PSCP system provides the 2D microscopic chemometric maps of absolute concentrations of native fluorescent molecules, enabling spatially resolved analysis of molecular activity and leading to significantly improved contrast. The spatially co-resolved tissue structure and molecular activities combining the high sensitivity of light scattering to the former and the high sensitivity of tissue native fluorescence to the latter may lead to more accurate cancer diagnosis and prognosis. This allows the PSCP approach to overcome major challenges faced by conventional pathology including inter- and intra-observer variations inherent in the subjective diagnosis and the difficulty of distinguishing aggressive cancers from indolent ones.

Furthermore, the PSCP approach can be applied to not only standard unstained formalin-fixed paraffin-embedded tissue sections but also fresh or frozen tissue sections without any prior tissue processing. It can achieve real-time diagnosis and be potentially adapted for in-vivo applications. PSCP provides a reliable adjunct or an independent system for rapid diagnostic and prognostic assessment.

It is estimated that more than 1.6 million men and women were diagnosed with cancer and more than a half million men and women died of cancer of all sites in 2012. Prostate cancer (PCa) is the most commonly diagnosed cancer in men. Diagnosis and prognosis of prostate tumors currently relies on the histopathologic evaluation of the biopsy together with clinical findings, such as clinical stage and prostate-specific antigen (PSA) to determine treatment. PCa is among cancers with a well-developed cancer grading system. The Gleason score (GS), the most widely used method of prostate cancer tissue grading today, is the single most important prognostic factor in PCa. It is one determinant of a patient's specific risk of dying due to PCa and strongly influences decisions regarding options for therapy.

The Gleason grading system is based upon the degree of loss of the normal glandular tissue architecture (i.e., shape, size and differentiation of the glands). The subjective microscopic determination of this loss of normal glandular structure caused by the cancer is represented by a Gleason grade (GG), a number ranging from 1 to 5, with 5 being the worst grade possible. The Gleason score (GS) is the sum of GG of the predominant and the next most predominant patterns within prostate cancer tissue. The majority of PCa patients are now diagnosed with tumors of GS 6 and 7. These tumors can take two distinct disease courses—indolent or highly aggressive, leading to death if not treated. Clinicians and patients choose a primary treatment modality based largely on the score, such as surgery, radiation therapy, or cryosurgery with the accompanying morbidity and compromised quality of life; or watchful waiting, risking life with delayed treatment. However, Gleason grading and its score is largely subjective. There exists the possibility of inter-observer as well as intra-observer variations, especially when based on the small thin needle core tissue samples obtained at biopsy. Objective sub-stratification of prostate cancer, in particular, GS 6 and 7 cancers, a prognostically heterogeneous group of tumors, indolent or aggressive groups is much desired. It has been shown that other factors including the amount of Gleason grades 4 and 5, the nuclear structure alteration, and cycle proliferation genes relate to the overall prognosis of the patient. Prostate tumor heterogeneity further complicates use of Gleason grading based on limited samples to evaluate patient prognosis.

Prediction of biologic behavior based on Gleason scores, especially in large volume or multifocal tumor, is limited by the scoring system, which has its own inherent difficulties due to reliance on the volume of tumor. A system that may utilize alternate clues, such as tissue microenvironment and physiological state, may compensate for the great heterogeneity in Gleason scores across individual tumors and prove a more reliable adjunct or even an independent system for diagnostic and prognostic assessment.

The PSCP system addresses these challenges. PSCP integrates quantitative tissue structural and molecular imaging for cancer diagnosis and prognosis for the first time to simultaneously quantify at the cellular/subcellular level important hallmarks of carcinogenesis, including alterations in the tissue microenvironment and cellular metabolism. The tissue microenvironment alterations accompanying carcinogenesis affect the spatial distribution of the refractive index of tissue, resulting in changes in its light scattering characteristics. PSCP uses light scattering to determine the sub-wavelength alterations in the microenvironment. Light scattering has been shown to be highly sensitive to the microarchitecture and composition of tissue and has been used to detect and evaluate sub-wavelength morphologic and biochemical changes in early carcinoma undetectable by other methods.

Quantitative phase imaging has concurrently emerged as a powerful light scattering technique to permit nanometer-scale measurements of structure and motion and to generate a spatially resolved sample scattering characteristics map in a noncontact, non-invasive manner. Another important hallmark of carcinogenesis is alterations in cellular metabolism. Cancer cell metabolism is often shifted from oxidative phosphorylation to aerobic glycolysis as the primary generator of cellular ATP. PSCP probes native fluorescent molecules and cellular metabolism based on auto-fluorescence of biological tissues. Auto-fluorescence has been demonstrated to be an effective probe for tissue physiological state. Monitoring cellular metabolism with auto-fluorescence has been successfully applied to differentiate normal, dysplasia, and cancer in vivo and ex vivo with high sensitivity and specificity.

The tight integration and co-registration of spatially resolved tissue structural and molecular imaging in PSCP offers significant advantages over existing approaches, such as digital pathology or auto-fluorescence spectroscopy. PSCP extracts objectively the inherent tissue sub-wavelength structural and molecular characteristics directly from light interaction with intact tissue, generating co-registered 2D microscopic maps of tissue morphology, mass distribution, scattering characteristics, and metabolism of biological tissue. PSCP also provides 2D microscopic chemometric maps of absolute concentrations of native fluorophores, enabling spatially resolved analysis of cellular metabolism and leading to significantly improved contrast. Test results indicate that tissue structural and molecular imaging complement each other and that the nuclear optical path length (OPL) and scattering characteristics are correlated closely with the aggressiveness of the cancer. The concentration of fluorophores and their ratios, as markers for cellular metabolism, also correlate closely with cancer grade. The combination of the high sensitivity advantage of light scattering to tissue structure and the high sensitivity advantage of co-registered native fluorescence to tissue physiological state (cellular metabolism in particular) in PSCP leads to more accurate cancer diagnosis and prognosis.

Furthermore, PSCP is label-free and achieves cost effective, objective real-time diagnosis and prognosis. In conventional approaches, the standard histopathological examination of the cancer biopsy requires multiple tissue processing steps. It is labor intensive and time consuming with frozen tissue preparation requiring 20-45 min for each tissue sample and routine permanent/fixed tissue sections typically requiring 12-18 hours processing and additional sectioning and staining steps. The time for expert manual assessment by conventional light microscopy may range from 5 minutes to 1 hour depending on the number of slides per specimen part. If there is diagnostic difficulty, immunohistochemistry may be required which can take an additional 24 hours to be performed and add a further 5 minutes to 1 hour for expert manual assessment. The cost for expert manual assessment may be determined based on salaries for a board qualified pathologist or by insurance charges for professional interpretation. In comparison, PSCP can be applied to not only the standard unstained formalin-fixed paraffin-embedded tissue sections but also fresh or frozen tissue specimens and hence eliminates the need for any prior tissue processing. The imaging speed of PSCP is mainly limited by the exposure time needed to record tissue native fluorescence images as the time for data processing utilizing currently available general purpose computer systems is minimal.

A complete PSCP scan can be completed within 2 to 3 minutes over 15 mm×15 mm area of a standard slide (under 20× objective) once the PSCP system is optimized and fully automated. This time can be further reduced using a more sensitive digital camera. The operating cost of PSCP is minimal compared to standard pathology once the system is purchased and setup. One significant advantage of a machine based system is that it will not suffer from day to day variations and will not be subject to human error missing a small focus on a slide. One advantageous use of PSCP is to prescreen the slides automatically and highlight suspicious regions and cases for further expert assessment to reduce the burden on pathologists. Another important advantage of PSCP lies in prognostication.

PSCP integrates quantitative spatially-resolved tissue structural and molecular imaging for the first time for objective cancer diagnosis and prognosis on intact tissue specimens, which simultaneously quantifies at the cellular and subcellular level important hallmarks of carcinogenesis. Varying tissue components differ in refractive index and render different extents of phase delay when light passes through. The quantitative phase map in PSCP may resolve nanometer axial optical path differences. Minute alterations in tissue structure, undetectable by the conventional pathology, are revealed. The tissue structure is quantified in detail beyond the scope of morphology. The cellular mass distribution is given by the phase map after scaling. The tissue scattering characteristics, such as the reduced scattering coefficient and the light scattering anisotropy factor maps computed via the scattering-phase theorem, are utilized to quantify the tissue local microenvironment signature. For example, a small "g" suggests that the size of the scattering tissue is small and the local region is more heterogeneous (such as fragmentation in nuclei) whereas a large "g" means that the size of the scattering tissue is large and the local region tends to be more homogenous. The nuclear OPL is a marker for the cell cycling rate. Both nuclear OPL and g have been found to correlate strongly with cancer aggressiveness. In addition, the co-registered chemometric imaging enables spatially resolved analysis of cellular metabolism, which leads to significantly improved contrast. As the tissue structural and molecular maps are complementary to each other, simultaneous measurement of both achieves higher accuracy in cancer diagnosis and prognosis in comparison to prior techniques.

Chemometric tissue native fluorescence imaging provides the co-registered 2D microscopic maps of absolute concentrations of native fluorescent molecules. The primary oxidation-reduction (redox) reactions in cells to generate energy in the form of ATP are the conversion of NAD+ to its reduced form NADH and the oxidation of flavin adenine dinucleotide (FAD) to FADH2, a process known as oxidative phosphorylation. Cancer cell metabolism is often shifted from oxidative phosphorylation to aerobic glycolysis as the primary generator of cellular ATP. This shift has long been known as the "Warburg effect" and results in a net increase in NADH. The tryptophan and NADH concentrations increase consistently as the cells progress from non-metastatic/low metastatic to metastatic state. These molecules including tryptophan, NADH and FAD are auto-fluorescent and hence tissue native fluorescence has been extensively investigated for diagnostic purposes. The challenges include: 1) tissue auto-fluorescence is weak and 2) auto-fluorescence is significantly modified by tissue morphology and hemoglobin absorption inside a bulk tissue. In PSCP, a RGB digital camera is used to record auto-fluorescence images of a slide containing a thin (e.g., approximately 4-5 microns thick) slice of tissue excited at UV and blue bands. The absolute concentration map of fluorophores is then computed with non-negative matrix factorization (NMF) of the measured RGB channels and system calibration. By avoiding averaging over the whole interrogated volume and providing spatially resolved concentrations of molecules, the contrast between tissues at different states is significantly enhanced. The shortcomings associated with the conventional tissue native fluorescence spectroscopy are thus addressed by PSCP, which possess the additional advantages a simple, label-free, real-time approach to chemometric mapping and metabolism assessment of the tissue section.

Co-registered quantitative tissue structural and molecular imaging together with a state-of-the-art support vector machine achieves high accuracy in cancer diagnosis and prognosis. Tissue structural and molecular imaging complements each other. Test results show that the nuclear OPL and g maps correlate strongly with biochemical recurrence of prostate cancer, whereas the optical metabolism parameters correlate more closely with cancer. The co-registered structural and molecular maps also open up novel avenues in data analysis to achieve more accurate risk scoring for patients. For example, the computation of fluorescence strength of native fluorophores may be refined by excluding the non-fluorescent nuclear region identified from the phase map. More importantly, the co-registered maps enable the characterization of morphology, mass distribution, scattering characteristics, and metabolism for each individual cell on the slide. The wealth of information on the tissue average characteristics, the single cell level statistics, and the spatial distribution characteristics are used as the input to a state-of-the-art support vector machine (SVM) to develop objective and accurate cancer risk scoring for patients. With these innovations, the performance of PSCP is expected to improve further over the already very promising preliminary results.

An illustrative PSCP microscopic imaging system may be implemented on an inverted epi-fluorescence differential interference contrast (DIC) microscope (Axiovert 40cfl, Zeiss). For quantitative phase imaging, the light source is a Halogen 35 W lamp filtered by narrow-band filters with wavelengths selectable from 400 nm to 700 nm at a step size of 50 nm and measurement at one single wavelength (500 nm) is normally used.

The numerical apertures for the condenser and objective (APlan) are 0.2 and 0.5, respectively. For epi-fluorescence measurement, the light source is a 50 W mercury arc lamp. The microscope is equipped with a focus drive (TOFRA, California). The DIC images are recorded by a low noise CCD camera (INFINITY2-1R, Lumenera) and fluorescence images are recorded by a digital camera (Canon 5D Mark II). A motorized stage may be used to scan the specimen. Custom codes in Matlab (Mathworks) may be utilized to automate the whole system from scanning and focusing the specimen, recording DIC and fluorescence images, to performing data analysis and finally risk-stratification of cancer.

More specifically, in an illustrative embodiment, the Halogen 35 W lamp is filtered by narrow-band filters with wavelengths selectable from 400 nm to 700 nm at a step size of 50 nm and measurement at one single wavelength (500 nm) is used. The numerical apertures for the condenser and objective (×40) is 0.2 and 0.5 respectively. For epi-fluorescence measurement, the light source is a 50 W mercury arc lamp. The microscope is equipped with a focus drive (TOFRA, California). The DIC images are recorded by a low noise CCD camera (INFINITY2-1R, Lumenera) and fluorescence images are recorded by a digital camera (Canon 5D Mark II). A motorized stage is used to scan the specimen. Custom codes in Matlab (Mathworks) automate the overall system from scanning/focusing the specimen, recording DIC and fluorescence images, to performing data analysis and finally risk-stratification of cancer.

A specific example is described below with theoretical development. FIG. 3 shows equation (1) relating to DIC imaging, which is valid where $I(\rho)$ is the DIC image, $k=2\pi n_0/\lambda$ is the wave number of the probing beam with $n_0$ the background refractive index and $\lambda$ the wavelength of light in vacuum, and $\phi(\rho)=k\int_0^L dz m(\rho,z)$ is the spatially resolved phase map for wave transmission through the thin slice of medium of thickness L with m the relative refractive index at position ($\rho,z$) with $\rho$ and z the lateral and axial coordinates, respectively. Transport of intensity equation (TIE) has been applied successfully for quantitative phase imaging with a brightfield microscope.

Equation (1) enables quantitative phase imaging with a DIC microscope. From Eq. (1), the Laplacian of the phase map can be approximated by Equation (2) shown in FIG. 4 where $I_0$ and $I_1$ are the in-focus and de-focus DIC images for the object, respectively, and the de-focus position is $\delta_z$ from the best-focus position. $\phi$ is solved from the Laplacian map $-\nabla_\perp^2 \phi$ using regularized Fourier transform. The optical path length (OPL) map is computed by OPL=$\phi(\rho)\lambda/2\pi$. The phase and OPL maps are proportional to the spatial distribution of cell mass from which the mass distribution is derived.

Tissue scattering is characterized by the scattering-phase relationship. A set of equations relates the scattering coefficient $\mu_s$, the reduced scattering coefficient $\mu'_s$, and the anisotropy factor g (normally 0<g<1 for tissue) of light scattering by a bulk turbid medium to the property of a phase map $\phi(\rho)$ of light transmission. These relationships are termed as the scattering-phase theorem equations (3), (4) and (5) shown in FIGS. 5, 6 and 7.

The scattering-phase theorem is applicable to a slice of homogeneous or inhomogeneous medium. In the latter case, a map of $\mu_s$, $\nu'_s$ and g are computed from the phase map using spatial averaging over the local region rather than the whole slice. The squared phase gradient map is computed by the finite difference of the phase map. A proper correction is applied for light diffraction in the microscope in the computation of the phase gradient.

The phase imaging in PSCP may be performed at one single wavelength (e.g., 500 nm) or at multiple wavelengths. When the phase imaging is measured at multiple wavelengths, the wavelength-dependent scattering characteristics can be used to compute the spectral slope of $\mu'_s$. The fractal dimension of the scattering structure can be computed from this spectral slope and there is a significant difference in fractal dimension between normal and cancerous tissue utilizing the discriminating power of the spectral slope and the fractal dimension derived from multiple wavelength phase measurements as additional input parameters to the SVM.

Referring to FIG. 8, a monolayer of polystyrene sphere suspension (size: 8.31 μm) in water and a thin film (thickness: 4 μm) of Intralipid-20% suspension (commonly used tissue phantom) on a glass microscope slide were imaged with the PSCP microscopic imaging system to produce a set of co-registered images 800. One pair of in-focus and out-of-focus ($\delta z=1$ μm) DIC images were taken for each specimen. The first column of images 802 show the optical path length maps for a monolayer of polystyrene sphere suspension (size: 8.31 μm) in water (top) and a thin film (thickness: 4 μm) of Intralipid-20% suspension (bottom). The second to sixth columns 804-812 show the H&E stained image, the in-focus DIC image, the OPL map, the reduced scattering $\mu'_s$ map, and the light scattering anisotropy factor g map for a case (A) of Gleason Score 8 (GS8) and PSA non-recurrence in 5 yrs (top row) and a case (B) of GS8 and PSA recurrence in 5 yrs (bottom row). The window size for the prostate cancer is 100 μm×100 μm. The stained and optical images are for different cut sections of the common site, and thus do not match exactly. The nuclear region is associated with high OPL values, high $\mu'_s$ mapvalues, and low g values in the respective maps. A has an average $\mu'_s$ mapof 0.027 μm$^{-1}$, the average optical path length over the nuclear region 0.85 μm, and the average nuclear g of 0.0914 whereas the corresponding values for B are 0.052 μm$^{-1}$, 1.50 μm, and 0.779, respectively. This is consistent with the general trend that higher $\mu'_s$, larger nuclear OPL and smaller nuclear g are observed for more aggressive cancer (see Table 3).

The first column 802 of images shows the computed OPL maps for the two samples. The scattering property for each individual spheres can be analyzed by applying the scattering-phase theorem to the region in the phase map occupied by the sphere. For example, the region highlighted by white dash lines for the central sphere yields $\mu_s$=0.234 μm$^{-1}$, $\mu'_s$=0.0202 μm$^{-1}$, and g=0.91 with an area 61.0 μm$^2$, corresponding to scattering and reduced scattering cross sections of 118 μm$^2$ and 10.2 μm$^2$, respectively. The mean scattering and reduced scattering cross sections for all the spheres contained in the section are 116 μm$^2$ and 9.8 μm$^2$, respectively. These values are in excellent agreement with the theoretical prediction for a polystyrene sphere of the specified size ($C_{sca}$=125 μm$^2$, $C'_{sca}$=9.5 μm$^2$ and g=0.92) at the probing wavelength 550 nm predicted by Mie theory.

Referring to table 900 shown in FIG. 9, the scattering and the reduced scattering coefficients for Intralipid-20% suspension are computed for the whole section after properly taking into account light diffraction in the microscope. Excellent agreement is also achieved between the measured and theoretical scattering properties for Intralipid-20% suspension. Table 900 shows a comparison between the theoretical scattering properties for polystyrene spheres and Intralipid-20% suspension with their measured values.

Specific contributing fluorophores for tissue native fluorescence include: aromatic amino acid residues found in most proteins ($\lambda_{ex}$=200-340 nm, $\lambda_m$=360-370, 455 nm); reduced pyridine nucleotides (NAD(P)H), which are cofactors in cellular metabolism and are found mainly in mitochondria, but are also present in the cytoplasm ($\lambda_{ex}$=360 nm, $\lambda_{em}$=460 nm); and flavins and flavin nucleotides (riboflavin, flavin mononucleotide, and dinucleotide), which are mostly bound to enzymes as coenzymes of flavoproteins and concentrated in the mitochondria ($\lambda_{ex}$=360,445-470 nm, $\lambda_{em}$=440,520 nm).

Endogenous porphyrins and age related lipofuscin have also been shown to be sources of cellular auto-fluorescence. Extracellular matrix components collagen and elastin also contribute strongly to tissue native fluorescence.

Referring to FIG. 10 showing equation (6), I is fluorescence intensity, w is weight factor and C is fluorophore content. The tissue native fluorescence intensity images will be recorded under UV excitation (for example using a DAPI/UV fluorescence filter set with the excitation wavelength centered at 365 nm with a bandwidth of 12 nm) and blue illumination (using a filter set with the excitation wavelength centered at 480 nm with a bandwidth of 40 nm) with a digital color camera. Each color image consists of three spectrally integrated fluorescence intensity maps in the R, G, and B channel, respectively. In general, the measured RGB channel image $I_i$ consists of contributions from the map $C_j$ produced by n species of fluorophores as shown in equation (6), where the weights $w_{ij} \geq 0$.

The weights are normalized by $\Sigma w_{ij}=1$ which ensures that the total fluorescence intensity map (summing over all channels from all excitations) produced by the jth component is $C_j$. The weights $w_{ij}$ can be regarded as the spectral signature of the jth component. The weights can be estimated from measurement of pure fluorescent components under the identical experimental condition noting that the weights may differ slightly between pure fluorophores and fluorophores in tissue owing to their different chemical environments. For example, a non-negative matrix factorization (NMF) of the measured RGB channels may be utilized to extract both the weights and the fluorescence map directly from the experimental data. The fluorescence map $C_j$ is then identified to be one of the main species of fluorophores with the spectral signature matching and a priori information on their spatial distribution characteristics. The absolute concentration and distribution of native fluorescent molecules is then given by $C_j/K_j$ where $K_j$ is a calibrated constant representing the total fluorescence intensity produced by one mole of the pure jth species of fluorophore under the identical experimental condition.

This chemometric microscopy quantifies the absolute concentration and distribution of native fluorophores including tryptophan, collagen, NADH, FAD, and porphyrin simultaneously for the first time. The redox ratios such as FAD/NADH and FAD/Tryptophan are obtained by dividing two respective concentration maps. The concentration ratio rather than the fluorescence intensity ratio may be reported as the former does not depend on the measurement condition. Note that strong signals from tryptophan may be observed from both the pure tryptophan sample and the tissue specimens under UV excitation although the illumination light is off its excitation peak (280 nm).

FIG. 11 shows the typical chemometric microscopy result for a pair of normal (top row) 1102 and cancerous (bottom row) 1104 unstained pathological slides of one GS7 prostate cancer patient, in addition to the corresponding stained image from a different serial cut section of the same site in the first column. The first column shows the corresponding stained image from a different serial cut section of the same site. The rest columns from left to right are the concentrations of tryptophan, NADH, FAD, the ratio of the concentration of FAD over that of tryptophan, and the ratio of the concentration of FAD over that of NADH, respectively. The window size is 62.5 µm×62.5 µm. Note the nuclei do not contain NADH or FAD. The average concentration of both tryptophan and NADH for the cancerous site is significantly higher than those of the normal site (tryptophan: 140 nM/mm$^3$ for the normal site and 740 nM/mm$^3$ for the cancerous site; NADH: 3 nM/mm$^3$ for the normal site and 7 nM/mm$^3$ for the cancerous site). The average concentration ratio drops from $4.3 \times 10^{-4}$ to $1.5 \times 10^{-4}$ for FAD/Tryptophan and from 0.023 to 0.015 for FAD/NADH, respectively, comparing the normal site to the cancerous site as shown table 1200 shown in FIG. 12. Table 1200 summarizes the difference measured for pairs of cancerous and adjacent normal prostate tissue from 19 patients. We observe that the cancerous region has higher concentration in Tryptophan and NADH ($p<0.01$) than the corresponding normal sites; the concentration ratios of FAD over Tryptophan or NADH is lower in the cancerous sites ($p<0.05$); and $\lambda'_s$ and OPL tend to decrease with cancer slightly yet the differences in their $\lambda'_s$, OPL, g, and the concentration of FAD are statistically insignificant. The same trends in the optical properties as shown in Table 1200 are also observed for this PCa cohort with the increase of the Gleason Score. The trends in Tryptophan and NADH concentrations and the redox ratios with the Gleason Score are, in general, statistically more significant, than the rest.

The optical parameters (including tissue average values and the single cell level statistics of at least nuclear OPL, the reduced scattering coefficient, the anisotropy factor, the native fluorophore concentration, and redox ratios) and the clinical parameters (Gleason scores and biochemical recurrence) obtained from both methods are collected and tabulated. The PSCP system correlates these factors with clinical detection of metastasis (usually by radiologic methods—bone scan or MRI/CT scan), and death of disease. The prolonged course of prostate cancer is such that PSA recurrence represents the earliest and most sensitive measure for disease recurrence and is the current standard for most studies. The clinical presence of metastases is an additional strong marker for aggressive disease. However in the clinical setting this is often not sought or documented in the face of ever rising PSA, which is sufficient evidence to warrant treatment. Although death from disease is tracked, these data are often unreliable in the absence of autopsy documentation. Nevertheless the system correlates results with all three markers of disease recurrence 1) PSA recurrence, 2) clinical evidence of metastasis, and 3) death of disease. By comparing the two sets of optical and clinical parameters, the correlation between them is established.

One unique advantage of using TMA and fresh cryopreserved prostate tissue sections from surgical specimens is that these samples are from large cohorts of prostate cancer cases with different Gleason scores and have follow up data covering a mean of 7 years post resection, essential for the development of the PSCP risk score for patient outcome. There is no statistically significant difference between the optical properties of fresh and cryopreserved tissue. Phase and native fluorescence measurement on 191 cases contained on a prostate cancer TMA cohort contains 19 adjacent normal sites, 65 GS6 sites, 82 GS7 sites, 23 GS8 sites, and 8 GS9 sites among which there are a total of 123 cases of PSA non-recurrence (NRec) and 44 cases of PSA recurrence (Rec) cases (either Gleason Score or PSA recurrence status of some cases is unknown).

Figures 12, 13, 14:
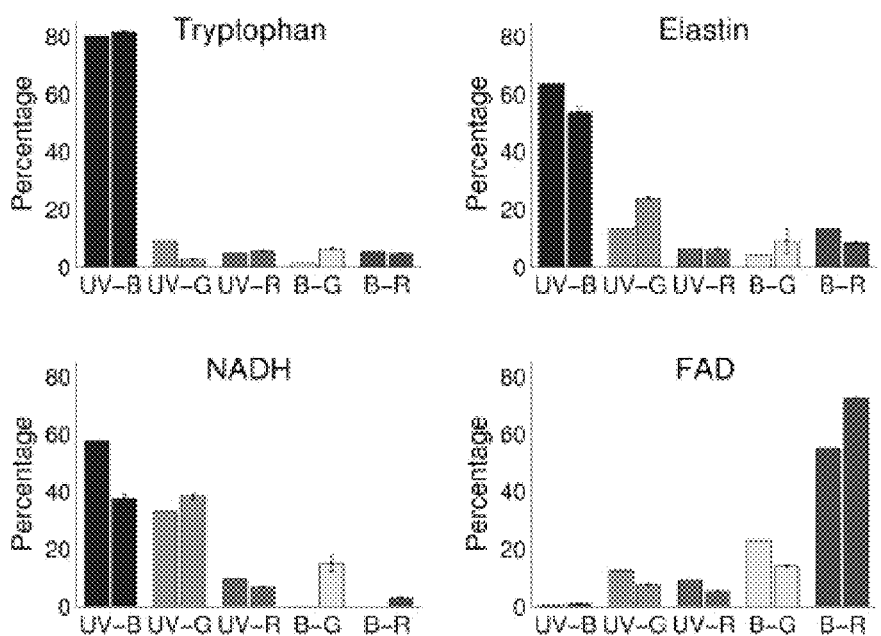
FIG. 12 shows a second table comparing image parameters for normal and cancerous images.
FIG. 13 shows a third table comparing image parameters for normal and cancerous images.
FIG. 14 shows comparison of spectra of "pure" fluorescence and extracted tissue fluorescence components.

Table 1300 of FIG. 13 includes shows both $\mu'_s$ and OPL are significantly higher and g is significantly lower in PSA Rec cases than PSA NRec cases (with p-values $p<10^{-3}$, $p<10^{-5}$ and $p<10^{-7}$ respectively) whereas no statistically significant difference is found for the concentrations of Tryptophan, NADH, and FAD, and the redox ratios FAD/Tryptophan and FAD/NADH, between the two groups consisting of 123 PSA NRec cases and 44 PSA Rec cases. The same trends of the optical properties of the site dependent on the PSA recurrence status as shown in Table 1300 are also observed within each individual Gleason Score group (not shown). This suggests that PSCP can sub-stratify prostate cancer into aggressive and non-aggressive subgroups.

The optical parameters presented in Tables 1200 and 1300 are tissue average characteristics. The single cell level statistics on these parameters may further reveal tissue structural and molecular alterations with cancer grade and aggressiveness and achieve even higher correlations between PSCP and the clinical parameters and patient outcome. This establishes a solid foundation for objective and accurate cancer risk scoring for patients.

A state-of-the-art support vector machine (SVM) technique may be utilized to develop the risk score for prostate cancer where the combination of SVM and a flow peaks algorithm yields high accuracy. The decision function (or discriminant function) from the trained SVM can be utilized as the risk score. When the outcome variable such as tumor grade has more than two categories, a one-against one approach may be applied to all possible two group comparisons.

Based on the correlation study on the cohorts of prostate cancer with the measured parameters, a PSCP risk score for prostate cancer from optically retrieved tissue structural and molecular maps is computed. The risk score may be based on the decision function of the support vector machine with the variables selected by recursive feature elimination. A SVM of the tissue average characteristics and the single cell level statistics on morphology, mass distribution, scattering properties, fluorophore concentrations, and their ratios will be carried out for different prediction problems. The algorithm differentiates prostate cancer from normal prostate including benign prostate hyperplasia, predicts tumor grade, and differentiates GS 6 from 7 tumors and sub-stratifies GS7 tumors. Based on this and information, the algorithm also assess cancer aggressiveness and predict patient outcome.

The system may also calculate receiver operator characteristics (ROC) curves and determine the diagnostic and prognostic performance using accuracy, sensitivity, and specificity for comparisons evaluated. A Gaussian kernel SVM of the tissue average characteristics alone may be computed by using the SVM functions. The accuracy, specificity and sensitivity are computed based on 10 random splits of five-fold cross-validations. The SVM using the Gleason score gives only 58.4±6.3 accuracy, 71.1±10.0 sensitivity, and 28.3±6.1 specificity. The best SVM utilizing a single variable can only achieve 69.6±1.2 accuracy, and all input variables 72.3±2.8 accuracy. Using the best subset of phase features selected by RFE including $\mu'_s$, nuclear OPL and g, the SVM achieves 79.5±1.3 accuracy, 79.5±1.5 sensitivity, and 79.3±5.2 specificity. By adding metabolism features, the SVM using the best subset of parameters selected by RFE yields accuracy 81.2±3.2, sensitivity 84.7±3.7, and specificity 73. 3±2.9. This preliminary result illustrates that the SVM utilizing carefully selected variables gives at least a ten-fold increase of accuracy over the best SVM utilizing a single variable and the inclusion of metabolism data is beneficial. The PSCP thus provides improvements in SVM, and more importantly, incorporates single-cell level statistics in addition to the tissue average characteristics into the SVM to produce a final risk scoring algorithm that achieves higher accuracy, sensitivity and specificity that prior approaches.

As another embodiment of the invention, the PSCP system is used for lung cancer tissue matrix array (TMA) (Biomax, USA) imaging. In this arrangement, the channels are UV-R, UV-G and UV-B (under the excitation of ultraviolet light), and are B-R and B-G (under the excitation of blue light). Under both of the above excitations, duration of exposure was fixed at 1.5 s. A set of aqueous suspensions containing a thin slice (~4 μm thick) of monolayer uniform pure fluorophores (comprising tryptophan, collagen, elastin, NADH, FAD and porphyrin) were prepared and measured individually under the identical experimental condition.

For each specimen, the spatially-resolved fluorescence image based on block principal pivoting NMF algorithm after background removal is the product of W and H. Distribution of a single fluorescence component is included in row H, and fluorescence species are determined by characteristic matrix W. FIG. 14 shows fluorescence component spectra obtained from measurement of a "pure" fluorescence bank and from resolving of tissue native fluorescence. Deviation bars indicate standard deviations of spectral signatures of fluorescence components extracted from all specimens. Differences between the extracted and the "pure" fluorescence spectra may be attributed to different chemical environments and to the difference between residuals resulted from NMF source separation. The spectral signatures of the extracted fluorescence components are generally consistent with those of the "pure" fluorescence bank.

Figures 15, 16:
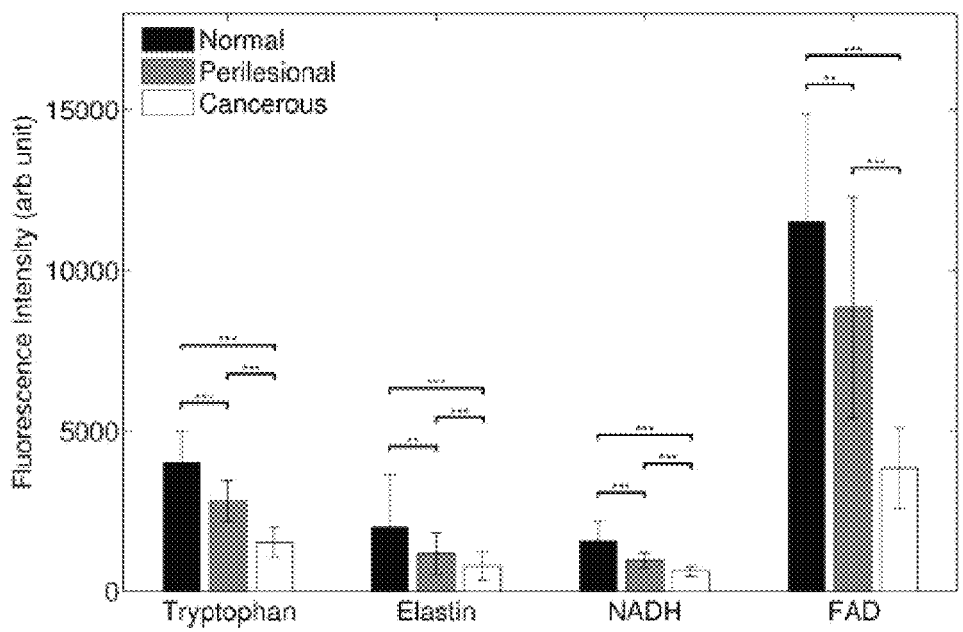
FIG. 15 shows the significant difference in absolute fluorescence intensity between different lung tissues.
FIG. 16 shows a fourth table comparing image parameters for normal and cancerous images.

Primary fluorescence species are determined to be Trp (tryptophan), elastin, NADH and FAD. The fluorescence intensities of the four main components differ significantly in normal lung tissue (n=26), perilesional tissue (n=34) and cancerous tissue (n=58) (in FIG. 15, the statistical significance of each of which is respectively represented by "*" (P=0.05), "" (P<0.01) and "*" (P<0.001)). Table 4 summarizes concentrations (mM) of tryptophan, elastin, NADH and FAD in normal, perilesional and cancerous tissues, as well as Redox ratios (concentration ratios) of FAD/tryptophan and FAD/NADH. Significant decrease in tryptophan, elastin, NADH and FAD concentration is observed from normal to perilesional lung tissues to cancer cells. The same trend is observed in Redox ratios (FAD/tryptophan and FAD/NADH) among perilesional normal lung tissues, which, however, exhibit no significant difference statistically.

Figure 17:
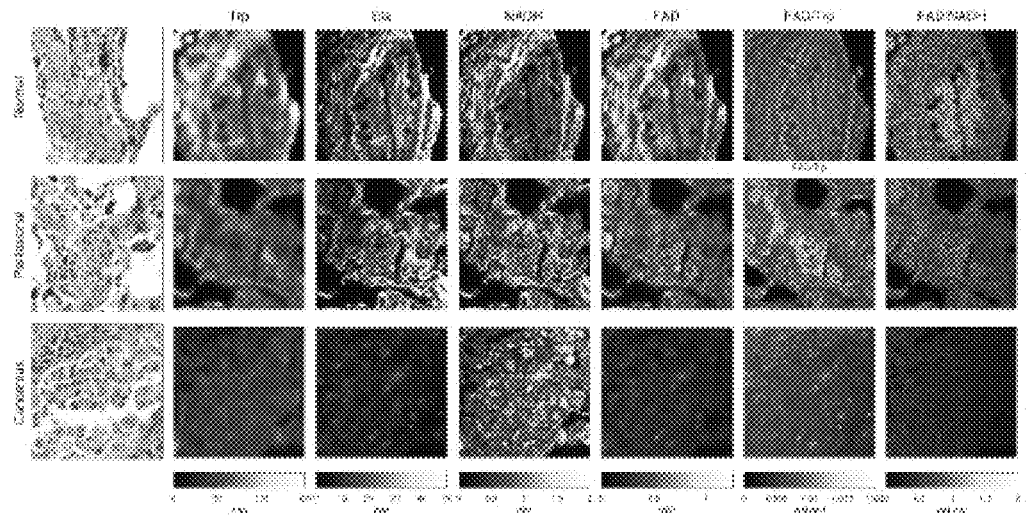
FIG. 17 shows resolved concentration maps for normality and lung cancer.

Typical results in the resolved concentration maps, as shown in FIG. 7, represent a normal lung tissue (top row), a perilesional tissue (middle row) and a cancerous tissue (bottom row). Average concentrations of tryptophan, elastin, NADH and FAD exhibit generally monotonic decrease from normal, focal to cancerous tissues (for tryptophan in normal, perilesional and lung cancer tissues: 61.7 mm, 40.6 mm and 34.6 mm, respectively; for elastin: 15.2 mm, 13.7 mm and 6.2 mm, respectively; for NADH: 0.61 mm and 0.67 mm, respectively; and for FAD: 0.47 mm, 0.35 mm and 0.20 mm, respectively). Corresponding average concentration ratios, for FAD/tryptophan, are 0.0065, 0.0085 and 0.0053, respectively, and for FAD/NADH, are 0.74, 0.56 and 0.31, respectively, in consistency with Table 4. Top row in FIG. 17 shows a corresponding H&E stained image from a different serial cut section of the same site. The window size is 160 μm×160 μm. There is a relevance between mitochondria and the increase in NADH and FAD concentrations. It is clearly shown from the "perilesional" that rich mitochondria exist in NADH, FAD and FAD/tryptophan maps.

Figure 18:
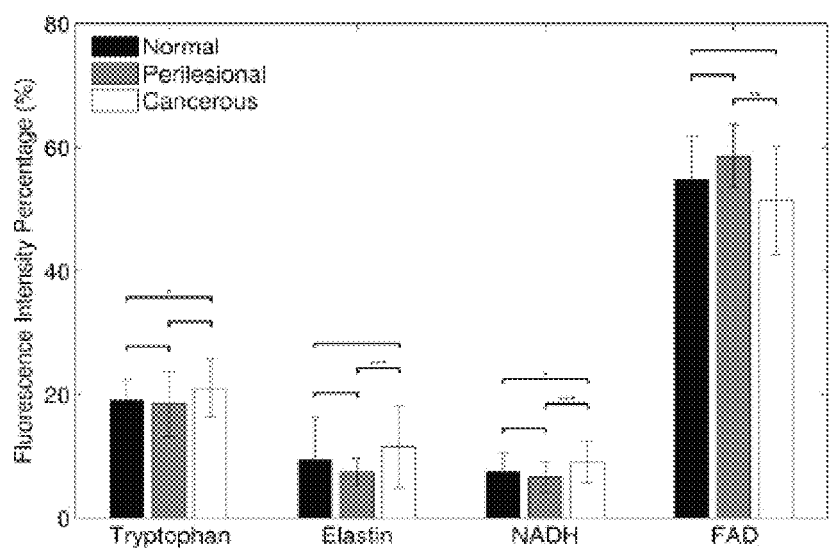
FIG. 18 shows a chart comparing fluorescence intensity percentages for normality and lung cancer.

Decrease in tryptophan concentration indicates accelerated decomposition and enhanced cell inducer degradation of tryptophan, similar to what is observed in serum of a patient with lung cancer. Elastin is found to be a main fluorescence in lung tissue. Compared with that in normal tissue, dramatic reduction of disordered fiberous web accompanied with fluorescence is observed in pre-cancerous lesion tissue. Pitzer, et al. found that cells transformed by cancerogenic substances exhibited obvious decrease in NADH and flavin and in dot fluorescence intensity, and that immortalized human bronchial epithelial cells lost spatial positioning of native fluorescence in comparison with human bronchial epithelial cells. The same trend is observed here (see Table 4 and FIG. 17). The decrease in FAD/NADH Redox ratio for cancer is a result of the globally-known Warburg effect. It is to be noted that, here, not only FAD and NADH in cancer but also the absolute concentration of FAD decreases more significantly than other fluorescent substances. It brings an increase in FAD/NADH Redox ratio and further observes the increase of NADH (and other non-FADs) percentage in the fluorescence (see FIG. 18) of overall detected signals. In lung tissue, the ratio of FAD/tryptophan exhibits a trend similar to the ratio of FAD/NADH.

A potential problem for NMF is that it may lead to a non-unique solution. Such fuzziness is minimized by utilizing spectral signatures of known pure "fluorescence" as initial conjecture for block principal pivoting NMF algorithm of the characteristic matrix. By measuring synthesized data with noise added, stability of this approach is verified. Due to their similar spectral signatures, the reduced NADH and FAD exhibit a difference less than 8% under a noise less than 5%, and the reduced tryptophan and protein exhibit a difference less than 20% under a noise approximating 2%. In our experiments, noise in the measured fluorescence images is 1%.

Figure 19:
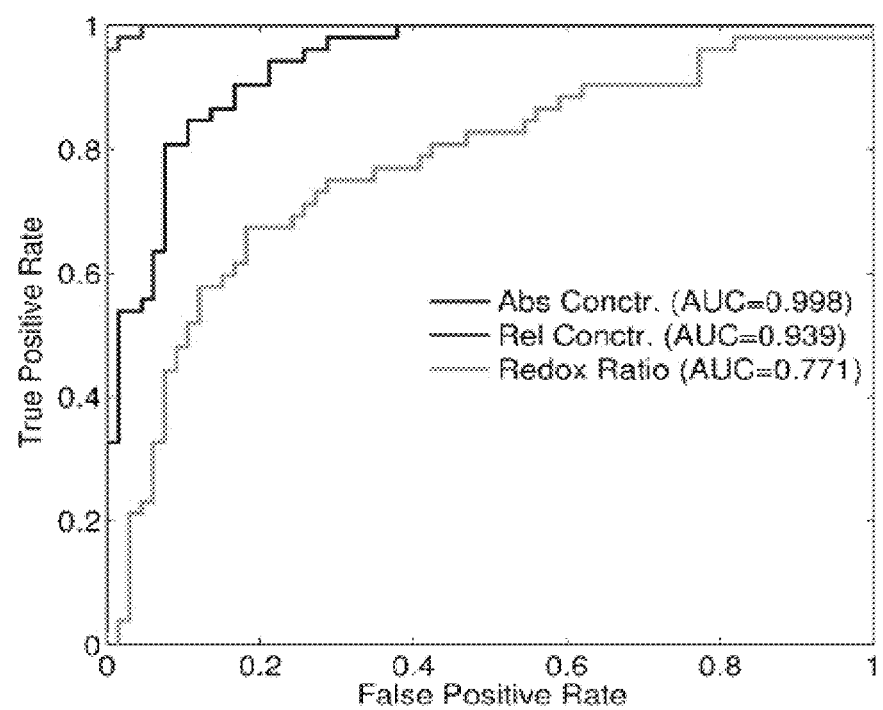
FIG. 19 shows ROC curves for normality and cancer.

There are some important benefits for obtaining absolute concentrations of fluorescence components instead of their relative content through individual quantization of fluorescence species. This eliminates potential uncertainty in system response and measurement details, which otherwise might influence the reported data and the observed fluorescence characteristics related to the physiological status of tissue. The objective comparison between different approaches is simplified. Most importantly, the absolute fluorophore concentration is recovered to be relevant biodata to facilitate data interpretation and tissue diagnosis improvement. Diagnosibility through relative fluorescence intensity is much weaker than that through absolute fluorescence component concentration. In fact, absolute concentrations can be used for classifying non-cancers (perilesional normalities, n=66) and tumors (n=52) more accurately than relative fluorescence intensity. The ROC graph shown in FIG. 19 computes five-fold cross-validations that use a support vector machine, wherein classification accuracy is 99.8% for the former, and is 93.9% for the latter. Accuracy for Redox ratio alone is 77.1%.

The embodiments illustrated above are for diagnosis of prostate cancer and lung cancer. However, the invention is not limited thereto. The above approaches not only generate good results in diagnosis and prognosis of prostate cancer and lung cancer, but also possess the ability to detect and prognose other cancers and other pathologies. In some embodiments, a method for quantifying a microstructure of a biological tissue by utilizing light interaction obtains a Q-DIC image by imaging a tissue section with a phase imaging microscope; and then analyzes the Q-DIC image, wherein the reduced scattering coefficient $\mu'_s$, optical path length OPL and anisotropy factor g obtained by the above equations 1-5 may be used for detection of human bodies and other living bodies, including but not limited to detection, diagnosis and prognosis of pathologies and cancers. In some embodiments, a method for quantifying a molecular content of a biological tissue by utilizing the auto-fluorescence thereof images a tissue section with a fluorescence imaging microscope to obtain a fluorescence microscope image, then compute the fluorescence microscope image by the above equation (6) to obtain an absolute concentration data map of fluorescence components, and then obtains data on tryptophan, collagen, NADH, FAD and porphyrin. The method can also be used for detection of human bodies and other living bodies, including but not limited to detection, diagnosis and prognosis of pathologies and cancers.

The invention claimed is:

1. A method for quantifying a microstructure of a biological tissue by utilizing light interaction, comprising steps of
   (1) imaging tissue sections with a phase imaging microscope to obtain a Q-DIC image, and
   (2) analyzing the Q-DIC image to obtain a two-dimensional Q-DIC quantitative map,
   in which step the Q-DIC image is computed by the following equations to obtain a reduced scattering coefficient $\mu'_s$, an optical path length OPL and an anisotropy factor g, and a two-dimensional map of spatial distribution of $\mu'_s$, OPL and g is the two-dimensional Q-DIC quantitative map:

$$k\frac{\partial I}{\partial z} = -I\nabla_\perp^2 \phi \quad \text{Equation (1)}$$

$$-\nabla_\perp^2 \phi = k\frac{\partial \ln I}{\partial z} = k\frac{\ln I_1 - \ln I_0}{\delta z} \quad \text{Equation (2)}$$

$$\mu_s L = 2\langle 1 - \cos\Delta\phi \rangle \quad \text{Equation (3)}$$

$$\mu'_s L = \frac{1}{2k^2}\langle |\nabla\phi|^2 \rangle \quad \text{Equation (4)}$$

$$OPL = \phi(\rho)\lambda/2\pi \quad \text{Equation (5)}$$

$$g = 1 - \frac{\langle |\nabla\phi|^2 \rangle}{4k^2\langle 1 - \cos\Delta\phi \rangle}, \quad \text{Equation (6)}$$

where $I(\rho)$ is the DIC image, $k=2\pi n_0/\lambda$ is the wave number of the probing beam with $n_0$ the background refractive index and $\lambda$ the wavelength of light in vacuum, $\phi(\rho)=k\int_0^L dz m(\rho, z)$ is the spatially resolved phase map for wave transmission through the thin slice of medium of a thickness L with m the relative refractive index at a position $(\rho, z)$ with $\rho$ and z the lateral and axial coordinates, respectively, $I_0$ and $I_1$ represent the in-focus and de-focus DIC images for the object, respectively, the de-focus position is $\delta z$ from the best-focus position, $\phi$ is obtained using Laplace transform, $-\nabla_\perp^2 \phi$ is obtained using regularized Fourier transform, $\mu_s$ is the scattering coefficient, $\mu'_s$ is the reduced scattering coefficient, and g is the anisotropy factor.

2. A method for quantifying a molecular content of a biological tissue by utilizing the auto-fluorescence thereof, comprising steps of
   (1) imaging native fluorescence of a tissue section with a fluorescence imaging microscope at multiple excitation wavelengths to obtain a fluorescence microscope image, and
   (2) computing and factorizing the fluorescence microscope image by the following equation to obtain a tissue native fluorescent component data map:

$$\begin{pmatrix} I_1 \\ I_2 \\ M \\ I_m \end{pmatrix} = \begin{pmatrix} w_{11} & w_{12} & \Lambda & w_{1n} \\ w_{21} & w_{22} & \Lambda & w_{2n} \\ M & M & O & M \\ w_{m1} & w_{m2} & \Lambda & w_{mn} \end{pmatrix} \begin{pmatrix} C_1 \\ C_2 \\ M \\ C_m \end{pmatrix},$$

where I is the fluorescence intensity, w is a weight factor, C is the content of a fluorescent substance, weight $w_{ij}$ can be regarded as the spectral signature of the jth component, the weights are normalized by $\Sigma_i w_{ij}=1$ to ensure that the total fluorescence intensity map produced by the jth component is $C_j$, the weights can be estimated from measurement of "pure" fluorescent components under the identical experimental condition noting that the weights may differ slightly between pure fluorescence and fluorophores in tissue owing to their different chemical environments, a non-negative matrix factorization (NMF) of the measured RGB channels may be utilized to extract both the weights and the fluorescence map directly from experimental data, the fluorescence map $C_j$ is identified to be one of the fluorescence species with the spectral signature matching and a priori information on their spatial distribution characteristics, and then the absolute concentration and distribution of fluorescent molecules is given by $C_j/K_j$, where $K_j$ a calibrated constant representing the total fluorescence, i.e. the fluorescence intensity produced by one mole of the pure jth component under the identical experimental condition, wherein the tissue native fluorescent component data map is the absolute concentration.

3. The method of claim 2, wherein the tissue native fluorescent component data map comprises tryptophan, collagen, NADH, FAD and porphyrin data maps.

4. A method for performing cancer diagnosis and prognosis on unlabeled pathology tissue sections by using a photonic structural and chemometric pathology system, comprising
   obtaining a tissue sample from a human patient,
   preparing an unlabeled pathology section from the tissue sample,
   obtaining a phase differential microscope (Q-DIC) image of the pathology section,
   computing one or more two-dimensional Q-DIC quantitative maps from the Q-DIC image,
   obtaining a fluorescence microscope image of the pathology section at multiple excitation wavelengths,
   computing a fluorescent component data map from the fluorescence microscope image,
   generating or obtaining a risk scoring methodology comprising correlations based on statistical analysis of a database of two-dimensional Q-DIC quantitative maps and fluorescent component data maps for subjects with known pathology, and
   applying the risk scoring methodology to the combination of the two-dimensional Q-DIC quantitative maps and the fluorescent component data maps to obtain a cancer diagnosis and prognosis for the patient based on the patient's tissue sample and the database of two-dimensional Q-DIC quantitative maps and fluorescent component data maps for subjects with known pathology.

5. The method of claim 4, wherein the Q-DIC image is computed by the following equations to obtain a reduced scattering coefficient $\mu'_s$, an optical path length OPL and an anisotropy factor g, and a two-dimensional map of spatial distribution of $\mu'_s$, OPL and g is the two-dimensional Q-DIC quantitative map:

$$k\frac{\partial I}{\partial z} = -I\nabla_\perp^2 \phi \qquad \text{Equation (1)}$$

$$-\nabla_\perp^2 \phi = k\frac{\partial \ln I}{\partial z} = k\frac{\ln I_1 - \ln I_0}{\delta z} \qquad \text{Equation (2)}$$

$$\mu_s L = 2\langle 1 - \cos\Delta\phi\rangle \qquad \text{Equation (3)}$$

$$\mu'_s L = \frac{1}{2k^2}\langle |\nabla\phi|^2\rangle \qquad \text{Equation (4)}$$

$$OPL = \phi(\rho)\lambda/2\pi \qquad \text{Equation (5)}$$

$$g = 1 - \frac{\langle |\nabla\phi|^2\rangle}{4k^2\langle 1 - \cos\Delta\phi\rangle}, \qquad \text{Equation (6)}$$

where $I(\rho)$ is the DIC image, $k=2\pi n_0/\lambda$ is the wave number of the probing beam with $n_0$ the a background refractive index and $\lambda$ the wavelength of light in vacuum, and $\phi(\rho)=k\int_0^L dz m(\rho,z)$ is the spatially resolved phase map for wave transmission through the thin slice of medium of a thickness L with m the relative refractive index at a position $(\rho,z)$, with $\rho$ and z the lateral and axial coordinates, respectively, $I_0$ and $I_1$ represent the in-focus and de-focus DIC image for the object, respectively, the de-focus position is $\delta z$ from the best-focus position, $\phi$ is obtained using Laplace transform, $-\nabla_\perp^2 \phi$ is obtained using regularized Fourier transform, $\mu_s$ is the scattering coefficient, $\mu'_s$ is the reduced scattering coefficient, and $\mu_s$ is the anisotropy factor.

6. The method of claim 4, wherein the fluorescence microscope image is computed and factorized by the following equation to obtain the fluorescent component data map:

$$\begin{pmatrix} I_1 \\ I_2 \\ M \\ I_m \end{pmatrix} = \begin{pmatrix} w_{11} & w_{12} & \Lambda & w_{1n} \\ w_{21} & w_{22} & \Lambda & w_{2n} \\ M & M & O & M \\ w_{m1} & w_{m2} & \Lambda & w_{mn} \end{pmatrix} \begin{pmatrix} C_1 \\ C_2 \\ M \\ C_m \end{pmatrix}; \qquad \text{Equation (6)}$$

where I is the fluorescence intensity, w is the weight factor, C is the content of a fluorescent substance, weight $w_{ij}$ can be regarded as the spectral signature of the jth component, and weights are normalized by $$\sum_i w_{ij} = 1$$

to ensure that the total fluorescence intensity map produced by the jth component is $C_j$, the weights can be estimated from measurement of "pure" fluorescent components under the identical experimental condition noting that the weights may differ slightly between pure fluorescence and fluorophores in tissue owing to their different chemical environments, a non-negative matrix factorization (NMF) of the measured RGB channels may be utilized to extract both the weights and the fluorescence map directly from the experimental data, the fluorescence map $C_j$ is identified to be one of the fluorescence species with the spectral signature matching and a priori information on their spatial distribution characteristics, and then the absolute concentration and distribution of fluorescent molecules is given by $C_j/K_j$, where $K_j$ is a calibrated constant representing the total fluorescence, i.e. the fluorescence intensity produced by one mole of the pure jth component under the identical experimental condition,
   wherein the tissue native fluorescent component data map is the absolute concentration.

7. The method of claim 4, wherein the fluorescent component data map comprises tryptophan, collagen, NADH, FAD and porphyrin data maps.

8. The method of claim 4, wherein the cancer is prostate cancer.

9. The method of claim 4, wherein the cancer is lung cancer.

* * * * *